United States Patent [19]

Horwath et al.

[11] 4,431,733

[45] Feb. 14, 1984

[54] PROCESS FOR PREPARING FRUCTOSE FROM LIQUEFIED STARCH

[75] Inventors: Robert O. Horwath, Westport; Robert M. Irbe, Norwalk, both of Conn.

[73] Assignee: Nabisco Brands, Inc., Parsippany, N.J.

[21] Appl. No.: 393,590

[22] Filed: Jun. 30, 1982

[51] Int. Cl.³ .................. C12P 19/24; C12P 19/20; C12N 9/92; C12R 1/645
[52] U.S. Cl. ..................................... 435/94; 435/96; 435/234; 435/911
[58] Field of Search .......................... 435/94, 234

[56] References Cited

U.S. PATENT DOCUMENTS 4,308,349  12/1981  Foley et al. .................. 435/234

OTHER PUBLICATIONS

Chemical Abstracts vol. 96: 17343u (1982).

Primary Examiner—Lionel M. Shapiro
Attorney, Agent, or Firm—R. Kornutik

[57] ABSTRACT

Process for preparing fructose from liquefied starch by contacting the liquefied starch with glucoamylase to hydrolyze said starch to glucose and contacting the glucose so produced with glucose isomerase to isomerize to least a part of the glucose to fructose. The glucoamylase and glucose isomerase are obtained from an organism of the Basidiomycetes class of fungi.

13 Claims, No Drawings

PROCESS FOR PREPARING FRUCTOSE FROM LIQUEFIED STARCH

BACKGROUND OF THE INVENTION

This invention relates to enzymatic processes for converting liquefied starch to glucose (dextrose) and for converting glucose (dextrose) to fructose (levulose).

Most food grade glucose is provided as an enzymatic hydrolysate of corn starch, i.e., the corn syrup of commerce. Glucose is generally rated at being 60 to 80% as sweet as sucrose and therefore sells at a correspondingly lower price. It has long been known to isomerize glucose to fructose which is even sweeter than sucrose by employing an enzyme having glucose isomerase activity, preferably one which has been immobilized upon an inert support such as diethylaminoethyl-cellulose, porous glass or chitin. The isomerization of glucose provides an equilibrium mixture typically containing 42-55% fructose and is referred to as high fructose corn syrup (HFCS).

It is known that glucoamylase and glucose isomerase can be isolated from a substantial number of microorganisms including species of Streptomyces, Bacillus, Nocardia, Lactobacillus, Ampullariella, and various other genera of microorganisms, and the enzymes have been employed in the commercial production of fructose from liquefied starch by known enzymatic techniques to provide mixtures of glucose and fructose. In the commercial process most commonly in present use, cornstarch is liquefied enzymatically or chemically, and then treated with glucoamylase to produce glucose which is thereafter isomerized using glucose isomerase to mixtures containing both fructose and glucose. Higher concentrations of fructose are particularly desirable and may be obtained by the use of more active enzymes and/or the use of high isomerization temperatures.

Detailed descriptions of the enzymatic conversion of glucose to fructose employing glucose isomerase can be found in Hamilton, et al. "Glucose Isomerase a Case Study of Enzyme-Catalyzed Process Technology," *Immobilized Enzymes in Food and Microbial Processes*, Olson et al., Plenum Press, New York, (1974), pp. 94–106, 112, 115–137; Chen, et al., "Glucose Isomerase (a Review)," *Process Biochem*, (1980), pp. 30–35; Chen, et al., "Glucose Isomerase (a Review)," *Process Biochem.*, (1980), pp. 36–41; Nordahl, et al., "Fructose Manufacture from Glucose by Immobilized Glucose Isomerase," *Chem. Abstracts*, vol. 82, (1975), Abs. No. 110316h; and Takasaki, "Fructose Production by Glucose Isomerase," *Chem. Abstracts*, vol 81, (1974), Abs. No. 76474a. In addition, there are numerous patents relating to glucose isomerization of which U.S. Pat. Nos. 3,616,221, 3,623,953 (U.S. Pat. No. 28,885), U.S. Pat. Nos. 3,694,313, 3,708,397, 3,715,276, 3,788,945, 3,909,354, 3,960,663, and 4,308,349 are representative.

Because of the economics involved in producing glucose isomerase, it is of the utmost importance to use the isomerase under conditions whereby maximum yields of fructose are produced using minimum quantities of glucose isomerase. Moreover, the conditions for isomerization should be such that minimal quantities of objectionable by-products are produced.

SUMMARY OF THE INVENTION

It has now been surprisingly discovered that fungi of the class Basidiomycetes produce significant quantities of glucoamylase and glucose isomerase. In particular, species of Irpex, Stereum, Perenniporia, Ramaricium, Sebacina, Lentinus, Coriolus and Panellus accumulate not only glucose isomerase activity which is produced in the mycelia of these organisms, but also glucoamylase which is extracellular and, therefore, accumulates in the nutrient medium. One can readily obtain a separation of the two enzymes by merely filtering the cells. The mycelia can be employed in the enzymatic reaction mixture as a source of glucose isomerase or the enzyme activity can be separated from the mycelia by known methods after harvesting the mycelia from the media in which grown. The glucose isomerase can be separated from the mycelia by the usual extraction techniques, e.g., using sonic treatment or chemical lysing. Of course, to avoid needless expense, the nutrient medium containing glucoamylase activity can be used as the source of the enzyme or, if desired, the enzyme can be separated from the nutrient medium by using known techniques, e.g., column adsorption of the nutrient medium containing enzyme followed by selective elution of the glucoamylase.

In addition to the aforementioned microorganisms, the present invention contemplates the use of mutants and variants thereof as well as genetically transformed microorganisms derived therefrom by introduction of the enzyme genes into other microorganisms, including mesophilic and preferably thermophilic microorganisms. In addition, the isolated genes can be mutated to improve the properties of the respective enzymes with which they are associated. For example, the glucose isomerase gene can be mutated. The mutated glucose isomerase genes selected for such use are those which provide glucose isomerase which is stable at elevated temperatures, especially above 90° C. and preferably up to about 110° C. Such genes can be prepared by the usual techniques used for mutation of microorganisms such as irradiation or chemical means. Thus, isolated glucose isomerase genes which produce glucose isomerase of moderate thermal stability, on *in vitro* mutagenesis will undergo mutation, and selection of the appropriate mutated genes is accomplished by reintroduction of the mutated gene into either the parent or other organism, preferably a thermophilic organism followed by replication of the organism and testing of the thermal stability of the resulting glucose isomerase.

DESCRIPTION OF THE PREFERRED EMBODIMENTS

Liquefied starch prepared by conventional means, such as those described in U.S. Pat. Nos. 3,654,081 and 3,663,369, is converted to glucose by enzymatic hydrolysis using glucoamylase produced by the microorganisms of the class Basidiomycetes. The glucose formed is thereafter converted to fructose by glucose isomerase produced by the same organism which produced the glucoamylase, i.e., the Basidiomycetes.

The liquefied starch starting material of this invention may be obtained from cereal grains such as corn, milo, wheat, rye, and the like, and amylaceous roots and tubers such as potatoes, yams, carrots, cassava (manioc), and the like. In the United States, corn starch is especially preferred due to its comparatively low cost and ready availability. Since the production of food grade glucose favors the use of enzymatic starch hydrolysis procedures, such procedures are preferred herein. Enzyme hydrolysis methods are described in U.S. Pat.

Nos. 4,017,363; 3,912,590; 3,922,196; 3,922,197-201 and 4,282,722, the disclosures of which are incorporated by reference herein.

Since the same microorganism produces both glucoamylase and glucose isomerase, fructose can be obtained from liquefied starch in a single batch reactor by the mere expediency of adding the Basidiomycetes mycelia to the original glucoamylase reactor or in a separate reactor after glucoamylase conversion is completed.

The liquefied starch is hydrolyzed to glucose by glucoamylase by procedures known to those familiar with the art. For example, the hydrolysis generally occurs at a somewhat lower temperature than the liquefication of starch, e.g., within the range of 55° C. to 60° C., at a pH between 4.0 and 5.0, with sufficient glucoamylase, and for about 15 to 75 hours to provide a glucose-containing solution of a high level of purity, e.g., 97–98% glucose.

Glucose can be isomerized to fructose in accordance with the present invention employing any of the known procedures, including contacting glucose solutions with whole cells, or passing the solutions through a bed contaning bound, or immobilized, glucose isomerase. Materials and procedures used for the immobilization of enzymes are well known and are described in a number of publications including Wang, et al., *Fermentation & Enzyme Technology*, John Wiley & Sons, Inc., New York (1979), pp. 318–318 and Kirk-Othmer, *Encyclopedia of Chemical Technology*, 3rd Ed., John Wiley & Sons, Inc., New York, (1980) Vol. 9, pp. 148–172, the disclosures of which are incorporated by reference herein.

Particularly preferred species of the aforesaid glucoamylase and glucose isomerase producing Basidiomycetes for use in the present invention include:

| Fungus | ATCC Number |
|---|---|
| *Stereum striatum* | 20633 |
| *Irpex mollis* | 20634 |
| *Lentinus edodes* | 20635 |
| *Perenniporia compacta* | 20636 |
| *Ramaricium albofdanescens* | 20637 |
| *Sebacina calcea* | 20638 |
| *Coreolus versicolor* | 20639 |
| *Panellus stipticus* | 20640 |

Cultures of strains of these preferred species of fungi have been deposited with the American Type Culture Collection where these organisms were accorded the indicated accession numbers, i.e., ATCC numbers.

The determination of other glucoamylase and glucose isomerase-producing fungi of the Basidiomycetes class can be carried out using simple test procedures. Cultures of the test organism are incubated for 7 days at 25° C. with vigorous shaking in a growth medium containing cornsteep liquor, magnesium sulfate, potassium phosphate, xylose and agar in shake flasks. The cells are then separated from the nutrient medium by known methods, e.g., filtration, and the nutrient medium is tested for glucoamylase activity by simply adding liquefied starch as a substrate to the nutrient medium and, subsequently, testing for the presence of glucose. The filtered mycelia are then checked for glucose isomerase activity using fructose determination methods such as the acid carbazole-cysteine test or xylulose determination methods, using gas chromatography or high pressure liquid chromatography (HPLC).

Using these test procedures, or obvious modifications thereof, various species of fungi can be tested to determine the presence of the desired enzyme activities.

The selected fungi can be grown in accordance with known methods of propagation. One such method employs xylose as a carbohydrate source as well as other ingredients usually present in such media such as corn steep liquor, inorganic salts and the like.

After growth for a sufficient period of time, e.g., to about 120 hours, the mycelia are harvested usually by filtration followed by washing with water buffered to a pH in the range of 6 to 7. The nutrient medium is reversed for glucoamylase activity or, if desired, the enzyme may be extracted from the nutrient medium. The glucose isomerase is then extracted from the mycelia by known physical or chemical procedures such as using sonication, cell homogenization, lytic enzymes, surfactants, etc. The extract may be passed through a Sephadex column (G-25). The enzyme extract can now be used in the isomerization reaction. Alternatively, as previously mentioned, the mycelia can be used as the source of the enzyme in the isomerization reaction.

In order to describe more clearly the nature of the present invention, a specific example will hereinafter be described. It should be understood, however, that this is done solely by way of example and is intended neither to delineate the scope of the invention nor limit the ambit of the appended claims.

EXAMPLE

Preparation of glucoamylase and glucose isomerase:
  *Lentinusedodes* ATCC 20635 was grown according to the following:
  A. Culture Maintenance:
    After incubating the cultures on malt agar slants for 7 days at 30° C., the isolates were inoculated into shaker flasks or maintained under refrigeration (about 10° C.).
  B. Shake Flash Propagation:
    Inoculation medium was made up as follows:

| Ingredient | % By Weight |
|---|---|
| Cornsteep liquor | 2.0 (d.b.) |
| Xylose | 5.0 |
| $KH_2PO_4$ | 0.1 |
| $MgSO_4\ 7H_2O$ | 0.15 |
| Agar | 0.4 |
| adjust | pH to 6.5 |

80 Ml aliquots of the above medium were placed in 500 ml Erlenmyer flasks together with 20 ml of a 25% glucose solution (sterilized) for the inoculum fermentation and the flasks were brought to 80% of their volume with water purified by reverse osmosis. Production flasks were similarly charged except no agar was added.

First Stage (test tube) Propagation

In a sterile hood, approximately one half of the mycelia from a slant is transferred with a metal loop to a test tube with 10 ml of the inoculation medium and about six 3-mm glass beads (sterile). The tubes are vortexed for 30–60 seconds or until the mycelia are dispersed. The tubes are then placed on a G-50 shaker at 200 rpm, 30° C., for 7 days.

Second stage (inoculum) Propagation

After 7 days, 5 ml are transferred to a 500 ml Erlenmeyer shake flask, and 1 ml is transferred into brain heart infusion to check sterility. These inoculation flasks are placed on a G-50 shaker at 200 rpm, 30° C., for 7 days.

Third stage (production) Propagation

After 7 days, 5 ml are transferred from the inoculation flask to several fermentation flasks. The fermentation flasks are placed on the G-50 shaker at 200 rpm, 30° C., for 9 days.

C. Harvesting Cell Biomass:

After the 9-day incubation period, the pH of each shake flask was measured; the cell biomass was filtered and washed twice with pH 7.0 phosphate buffer. After the second filtration, the harvested cell biomass from each culture was weighed and frozen for bioconversion.

The nutrient medium containing the glucoamylase was dialyzed against maleate buffer 50 mm, pH 6.7, plus $CaCl_2$ 10 mm, for 15 hours at 40° C. with 3 changes.

Hydrolysis of liquefied starch to glucose:

Liquefied starch, prepared in accordance with U.S. Pat. No. 4,017,363 was hydrolyzed to glucose by employing the glucoamylase obtained above at about 60° C. at pH 4.5.

Isomerization of glucose to fructose:

Whole-cell Bioconversion:

(under sterile conditions) Approximately 1 gram wet weight cells is placed into a 300 ml baffled flask containing 50 ml of glucose phosphate buffer (1% glucose added to the phosphate buffer w/v) and the suspension made 0.02 M in NaF. The flask is placed on the G-50 shaker at 200 rpm, and samples are taken at 6, 12, and 24 hours by aseptically transferring 2 ml from the bioconversion flask to 15 ml Corning centrifuge tubes. The samples are centrifuged for 5 min. then, 1 ml is removed and passed through a Sep-Pak $C_{18}$ cartridge (Waters Associates, Milford Ma.) following which the filtrates were analyzed by high pressure liquid chromatography (HPLC).

Bioconversion by Cell-free Extracts:

Mycelia (4 g. wet weight) in phosphate buffer (pH 6.5) are blended in a Waring blender at low speed for 15 seconds. The buffered homogenate is then transferred to a 50 ml. glass Duran Sample Flask containing 50 g. (about 80% by volume) glass beads of a diameter of 0.45 to 0.5 mm. The chamber is then vigorously agitated with a Braun Mechanical Cell for 1 minute while cold carbon dioxide is allowed to flow past the chamber to minimize heating.

Alternatively, the low speed blended mycelia in buffer is placed in a plastic centrifuge tube in an ice bath and then sonicated with a Heat Systems Ultrasonics Cell Disrupter, Model 350, set at 50% duty cycle, output control at 6, continuous mode, in 5 cycles of 15 seconds on and 15 seconds off.

The extracts were filtered free of the mycelia

The isomerization mixture containing 10% of glucose (maleate buffered to pH 6.7), $MgCl_2$ (10 mM), $Co^{+2}$ (1 mM) and enzyme solution (50 mg of protein) obtained above was incubated at 60° C. for 3 hours.

The reaction mixture was then heated in a boiling water bath and the precipitated protein removed by centrifugation.

Assay of the mixture, actually aliquots thereof, showed the presence of fructose in addition to glucose. The assays employed were gas chromatography and the cysteine carbazole reaction.

We claim:

1. The process for preparing fructose which comprises contacting liquefied starch with glucoamylase to hydrolyze said starch to glucose and contacting the glucose so produced with glucose isomerase to isomerize at least a part of the glucose to fructose wherein said glucoamylase and glucose isomerase are obtained from an organism of the Basidiomycetes class of fungi.

2. The process of claim 1 wherein the organism is a species of Stereum, Irpex, Lentinus, Perenniporia, Ramaricium, Sebacina, Coriolus and Pannellus.

3. The process of claim 2 wherein the organism is *Stereum striatum* ATCC No. 20633.

4. The process of claim 2 wherein the organism is *Irpex mollis* ATCC No. 20634.

5. The process of claim 2 wherein the organism is *Lentinus edodes* ATCC No. 20635.

6. The process of claim 2 wherein the organism is *Perenniporia compacta* ATCC No. 20636.

7. The process of claim 2 wherein the organism is *Ramaricium albofdanescens* ATCC No. 20637.

8. The process of claim 2 wherein the organism is *Sebacina calcea* ATTC No. 20638.

9. The process of claim 2 wherein the organism is *Coriolus versicolor* ATCC No. 20639.

10. The process of claim 2 wherein the organism is *Pannellus stipticus* ATCC No. 20640.

11. The process of claim 1 wherein the glucoamylase activity is present in the nutrient medium employed for growth of the said organism.

12. The process of claim 1 wherein the glucose isomerase activity is present in the mycelia of the said organism.

13. The process of claim 12 wherein the glucose isomerase activity is extracted from the mycelia of the said organism.

* * * * *